United States Patent
Secrest et al.

(10) Patent No.: US 11,864,742 B2
(45) Date of Patent: Jan. 9, 2024

(54) BIOPSY DEVICE

(71) Applicant: UNITED STATES ENDOSCOPY GROUP, INC., Mentor, OH (US)

(72) Inventors: Dean Secrest, Concord Township, OH (US); Keith R. John, Chardon, OH (US)

(73) Assignee: United States Endoscopy Group, Inc., Mentor, OH (US)

(*) Notice: Subject to any disclaimer, the term of this patent is extended or adjusted under 35 U.S.C. 154(b) by 730 days.

(21) Appl. No.: 15/902,781

(22) Filed: Feb. 22, 2018

(65) Prior Publication Data

US 2018/0177496 A1  Jun. 28, 2018

Related U.S. Application Data

(63) Continuation of application No. 13/070,741, filed on Mar. 24, 2011, now abandoned.

(60) Provisional application No. 61/317,036, filed on Mar. 24, 2010.

(51) Int. Cl.
*A61B 10/04* (2006.01)
*A61B 10/06* (2006.01)
*A61B 10/02* (2006.01)

(52) U.S. Cl.
CPC ............ *A61B 10/04* (2013.01); *A61B 10/06* (2013.01); *A61B 2010/0225* (2013.01)

(58) Field of Classification Search
CPC .. A61B 10/04; A61B 10/06; A61B 2010/0225
See application file for complete search history.

(56) References Cited

U.S. PATENT DOCUMENTS

| | | |
|---|---|---|
| 2,751,908 A | 6/1956 | Wallace |
| 3,807,406 A | 4/1974 | Rafferty et al. |
| 3,964,468 A | 6/1976 | Schulz |
| 4,122,856 A | 10/1978 | Mosior et al. |
| 4,445,509 A | 5/1984 | Auth |
| 4,522,206 A | 6/1985 | Whipple et al. |
| 4,632,110 A | 12/1986 | Sanagi |
| 4,662,371 A | 5/1987 | Whipple et al. |
| 4,674,502 A | 6/1987 | Imonti |
| 4,693,257 A | 9/1987 | Markham |

(Continued)

FOREIGN PATENT DOCUMENTS

| | | |
|---|---|---|
| EP | 1063921 | 9/1999 |
| JP | 2000271128 A | 10/2000 |

(Continued)

OTHER PUBLICATIONS

Communication Pursuant to Rule 94(3) from European Patent Application No. 11760205.2 dated Oct. 11, 2018.

(Continued)

*Primary Examiner* — Rene T Towa
(74) *Attorney, Agent, or Firm* — Calfee, Halter & Griswold LLP

(57) ABSTRACT

A biopsy device includes a first jaw and a second jaw pivotally connected to the first jaw through a pivot. The second jaw has a lever arm extending rearward from the pivot when the second jaw is closed. A wire having an end is connected to the lever arm of the second jaw. A suction tube is disposed between the first and second jaw.

10 Claims, 13 Drawing Sheets

(56) References Cited

U.S. PATENT DOCUMENTS

| | | | |
|---|---|---|---|
| 4,712,545 A * | 12/1987 | Honkanen | A61B 17/1608 |
| | | | 606/208 |
| 5,108,381 A | 4/1992 | Kolozsi | |
| 5,217,460 A | 6/1993 | Knoepfler | |
| 5,286,255 A | 2/1994 | Weber | |
| 5,300,087 A | 4/1994 | Knoepfter | |
| 5,310,406 A | 5/1994 | Sharpe et al. | |
| 5,347,991 A | 9/1994 | Nakao et al. | |
| 5,373,854 A | 12/1994 | Kolozsi | |
| 5,383,471 A | 1/1995 | Funnell | |
| 5,417,709 A | 5/1995 | Slater | |
| 5,441,503 A | 8/1995 | Considine et al. | |
| 5,458,112 A | 10/1995 | Weaver | |
| 5,478,347 A | 12/1995 | Aranyi | |
| 5,571,136 A | 11/1996 | Weaver | |
| 5,575,293 A | 11/1996 | Miller et al. | |
| 5,603,724 A | 2/1997 | O'Connor | |
| 5,620,415 A * | 4/1997 | Lucey | A61B 17/1608 |
| | | | 606/205 |
| 5,665,100 A | 9/1997 | Yoon | |
| 5,669,394 A | 9/1997 | Bergey et al. | |
| 5,683,359 A | 11/1997 | Farkas et al. | |
| 5,683,388 A | 11/1997 | Slater | |
| 5,697,949 A * | 12/1997 | Giurtino | A61B 18/1445 |
| | | | 606/205 |
| 5,715,832 A | 2/1998 | Koblish et al. | |
| 5,775,333 A | 7/1998 | Burbank et al. | |
| 5,810,876 A | 9/1998 | Kelleher | |
| 5,817,033 A | 10/1998 | Desantis et al. | |
| 5,857,997 A * | 1/1999 | Cimino | A61B 5/0422 |
| | | | 604/95.01 |
| 5,871,453 A | 2/1999 | Banik et al. | |
| 5,871,454 A | 2/1999 | Majlessi | |
| 5,897,507 A | 4/1999 | Kortenbach et al. | |
| 5,906,629 A | 5/1999 | Oren et al. | |
| 5,928,164 A | 7/1999 | Burbank et al. | |
| 5,944,673 A | 8/1999 | Gregoire et al. | |
| 5,964,716 A | 10/1999 | Gregoire et al. | |
| 5,971,939 A | 10/1999 | Desantis et al. | |
| 5,980,468 A | 11/1999 | Zimmon | |
| 6,017,316 A | 1/2000 | Ritchart et al. | |
| 6,019,733 A | 2/2000 | Farascioni | |
| 6,053,933 A | 4/2000 | Balazs et al. | |
| 6,066,102 A | 5/2000 | Townsend | |
| 6,071,248 A | 6/2000 | Zimmon | |
| 6,074,408 A | 6/2000 | Freeman | |
| 6,106,543 A | 8/2000 | Esser | |
| 6,110,127 A | 8/2000 | Suzuki | |
| 6,139,508 A * | 10/2000 | Simpson | A61B 10/06 |
| | | | 606/205 |
| 6,142,956 A | 11/2000 | Kortenbach et al. | |
| 6,142,957 A * | 11/2000 | Diamond | A61B 10/0266 |
| | | | 600/567 |
| 6,162,187 A | 12/2000 | Buzzard et al. | |
| 6,174,292 B1 | 1/2001 | Kortenbach et al. | |
| 6,282,442 B1 | 8/2001 | Destefano et al. | |
| 6,309,404 B1 * | 10/2001 | Krzyzanowski | A61B 10/06 |
| | | | 606/205 |
| 6,322,522 B1 | 11/2001 | Zimmon | |
| 6,331,165 B1 | 12/2001 | Turturro et al. | |
| 6,358,224 B1 | 3/2002 | Tims et al. | |
| 6,387,057 B1 | 5/2002 | Heske | |
| 6,398,741 B2 | 6/2002 | Niizeki et al. | |
| 6,485,436 B1 | 11/2002 | Truckai et al. | |
| 6,530,891 B2 | 3/2003 | Miller | |
| 6,544,194 B1 | 4/2003 | Kortenbach et al. | |
| 6,569,105 B1 * | 5/2003 | Kortenbach | A61B 10/06 |
| | | | 600/562 |
| 6,599,309 B1 | 7/2003 | Gilman | |
| 6,613,068 B2 * | 9/2003 | Ouchi | A61B 10/06 |
| | | | 606/170 |
| 6,620,111 B2 | 9/2003 | Stephens et al. | |
| 6,632,182 B1 | 10/2003 | Treat | |
| 6,638,235 B2 | 10/2003 | Miller et al. | |
| 6,746,462 B1 | 6/2004 | Selmon et al. | |
| 6,832,990 B2 | 12/2004 | Kortenbach et al. | |
| 6,858,014 B2 | 2/2005 | Damarati | |
| 6,875,182 B2 | 4/2005 | Wardle et al. | |
| 6,878,149 B2 | 4/2005 | Gatto | |
| 6,926,676 B2 | 8/2005 | Turturro et al. | |
| 7,108,660 B2 | 9/2006 | Stephens et al. | |
| 7,118,586 B1 | 10/2006 | Paternuosto | |
| RE39,415 E | 11/2006 | Bales | |
| 7,169,115 B2 | 1/2007 | Nobis et al. | |
| 7,189,206 B2 | 3/2007 | Quick et al. | |
| 7,204,811 B2 | 4/2007 | Kortenbach et al. | |
| 7,220,226 B2 | 5/2007 | Rovegno | |
| 7,226,424 B2 | 6/2007 | Ritchart et al. | |
| 7,276,032 B2 | 10/2007 | Hibner | |
| 7,297,121 B2 | 11/2007 | Turturro et al. | |
| 7,322,935 B2 | 1/2008 | Palmer et al. | |
| 7,331,930 B2 | 2/2008 | Faciszewski | |
| 7,347,828 B2 | 3/2008 | Francese et al. | |
| 7,361,174 B2 | 4/2008 | Bee et al. | |
| 7,481,817 B2 | 1/2009 | Sauer | |
| 7,517,321 B2 | 4/2009 | McCullough et al. | |
| 7,559,887 B2 | 7/2009 | Dannan | |
| 7,569,626 B2 | 8/2009 | Truckai | |
| 7,572,236 B2 | 8/2009 | Quick et al. | |
| 7,762,960 B2 | 7/2010 | Timberlake et al. | |
| 7,833,167 B2 | 11/2010 | Kortenbach et al. | |
| 2002/0029006 A1 | 3/2002 | Turturro | |
| 2002/0029007 A1 | 3/2002 | Bryan et al. | |
| 2002/0173699 A1 | 11/2002 | Becker et al. | |
| 2003/0060816 A1 | 3/2003 | Koji | |
| 2003/0125639 A1 | 7/2003 | Fisher et al. | |
| 2004/0068291 A1 * | 4/2004 | Suzuki | A61B 10/04 |
| | | | 606/205 |
| 2004/0097829 A1 | 5/2004 | McRury et al. | |
| 2004/0153003 A1 | 8/2004 | Cicenas et al. | |
| 2005/0027210 A1 | 2/2005 | Miller | |
| 2005/0043758 A1 | 2/2005 | Golden | |
| 2005/0065453 A1 | 3/2005 | Shabaz et al. | |
| 2005/0113715 A1 | 5/2005 | Schwindt et al. | |
| 2005/0124913 A1 | 6/2005 | Damarati | |
| 2005/0165329 A1 | 7/2005 | Taylor et al. | |
| 2005/0187489 A1 | 8/2005 | Wardle et al. | |
| 2005/0245841 A1 * | 11/2005 | Turturro | A61B 10/0266 |
| | | | 600/562 |
| 2006/0178560 A1 | 8/2006 | Saadat et al. | |
| 2006/0258955 A1 | 11/2006 | Hoffman et al. | |
| 2007/0027407 A1 | 2/2007 | Miller | |
| 2007/0032723 A1 | 2/2007 | Glossop | |
| 2007/0038146 A1 | 2/2007 | Quick et al. | |
| 2007/0156064 A1 | 7/2007 | Ritchart et al. | |
| 2007/0167868 A1 | 7/2007 | Sauer | |
| 2007/0179401 A1 | 8/2007 | Hibner | |
| 2007/0213634 A1 | 9/2007 | Teague | |
| 2007/0270894 A1 | 11/2007 | Zimmon | |
| 2008/0009857 A1 * | 1/2008 | Yanuma | A61B 18/1445 |
| | | | 606/46 |
| 2008/0108871 A1 | 5/2008 | Mohr | |
| 2008/0221480 A1 | 9/2008 | Hibner et al. | |
| 2008/0255424 A1 | 10/2008 | Durgin et al. | |
| 2009/0149746 A1 | 6/2009 | Chernomorsky et al. | |
| 2009/0171147 A1 | 7/2009 | Lee et al. | |
| 2009/0182198 A1 | 7/2009 | Skerven et al. | |
| 2009/0187146 A1 | 7/2009 | Landman et al. | |
| 2009/0192352 A1 | 7/2009 | Regadas | |

FOREIGN PATENT DOCUMENTS

| | | |
|---|---|---|
| WO | 199519145 | 7/1995 |
| WO | 199840015 | 9/1998 |
| WO | 199945847 | 9/1999 |
| WO | 1999059475 | 11/1999 |
| WO | 2000054658 | 9/2000 |

(56) References Cited

OTHER PUBLICATIONS

Office Action from U.S. Appl. No. 13/070,741 dated Mar. 1, 2013.
Response to Office Action from U.S. Appl. No. 13/070,741 dated Jul. 1, 2013.
Office Action from U.S. Appl. No. 13/070,741 dated Sep. 12, 2013.
Response to Office Action from U.S. Appl. No. 13/070,741 dated Feb. 12, 2014.
Office Action from U.S. Appl. No. 13/070,741 dated May 29, 2014.
Response to Office Action from U.S. Appl. No. 13/070,741 dated Nov. 25, 2014.
Office Action from U.S. Appl. No. 13/070,741 dated Feb. 23, 2015.
Response to Office Action from U.S. Appl. No. 13/070,741 dated Aug. 21, 2015.
Office Action from U.S. Appl. No. 13/070,741 dated Sep. 11, 2015.
Response to Office Action from U.S. Appl. No. 13/070,741 dated Jan. 11, 2016.
Office Action from U.S. Appl. No. 13/070,741 dated Mar. 2, 2016.
Response to Office Action from U.S. Appl. No. 13/070,741 dated May 24, 2016.
Office Action from U.S. Appl. No. 13/070,741 dated Jul. 7, 2016.
Response to Office Action from U.S. Appl. No. 13/070,741 dated Sep. 8, 2016.
Office Action from U.S. Appl. No. 13/070,741 dated Oct. 7, 2016.
Response to Office Action from U.S. Appl. No. 13/070,741 dated Feb. 7, 2017.
Office Action from U.S. Appl. No. 13/070,741 dated Mar. 10, 2017.
Response to Office Action from U.S. Appl. No. 13/070,741 dated May 10, 2017.
Office Action from U.S. Appl. No. 13/070,741 dated May 18, 2017.
Response to Office Action from U.S. Appl. No. 13/070,741 dated Sep. 18, 2017.
Office Action from U.S. Appl. No. 13/070,741 dated Nov. 22, 2017.
European Search Report from European Patent Application No. 11760205.2 dated Nov. 15, 2017.
International Search Report and Written Opinion of the Korean Intellectual Property Office; Corresponding PCT Application PCT/US2011/029772; Authorized Officer: Won, Jong Hyuk; dated Jan. 2, 2012 (12 pages).

\* cited by examiner

BIOPSY DEVICE

CROSS-REFERENCE TO RELATED APPLICATIONS

This application is a continuation-in-part of U.S. Non-Provisional patent application Ser. No. 13/070,741, entitled "Multiple Biopsy Device," filed Mar. 24, 2011, which claims priority to U.S. Provisional Application No. 61/317,036 filed Mar. 24, 2010, the entirety of which are incorporated herein by reference.

FIELD OF INVENTION

The present application relates to a biopsy device. More particularly, the present application relates to an endoscopic biopsy device configured to take multiple tissue samples.

BACKGROUND

Endoscopic biopsy procedures may be performed with an endoscope and an endoscopic biopsy forceps device. The endoscope is a long flexible tube with various optical features allowing for visualization and having a narrow lumen through which the biopsy forceps device is inserted. Known biopsy forceps devices for endoscope use include a long flexible cannula having a pair of opposed jaws at the distal end and manual actuation means at the proximal end. Manipulation of the actuation means opens and closes the jaws.

During a biopsy tissue sampling operation, an operator guides the endoscope to the biopsy site while viewing a video image of the site. When the device is inserted into the endoscope with the opposed jaws extending from the narrow lumen of the scope, the operator can position the jaws around a tissue to be sampled and manipulate the actuation means so that the jaws close around the tissue. The normal closing action of the jaws may sever a tissue sample and in some cases, the operator may need to apply an additional pulling or closing force to sever a tissue sample. In one known single biopsy embodiment, the operator must first deliver the jaws to the tissue site via the endoscope lumen, sever the tissue sample with the jaws, withdraw the biopsy forceps device from the endoscope, and open the jaws to collect the single biopsy tissue sample from within.

With the single biopsy embodiment, the device must be repeatedly inserted, actuated, and withdrawn to acquire multiple tissue samples in a one-at-a-time manner. In another known embodiment of a multiple biopsy device, suction is used to retrieve the tissue sample while the distal end of the biopsy forceps device remains in the patient. In yet another embodiment, a suction passage is added to the biopsy device so that each biopsy sample can be withdrawn out of from the patient and retrieved from outside of the patient without withdrawing the instrument.

SUMMARY

A biopsy device includes a first jaws and a second jaw pivotally connected to the first jaw through a pivot. The second jaw has a lever arm extending rearward from the pivot when the second jaw is closed. A wire having an end is connected to the lever arm of the second jaw. A suction tube is disposed between the first and second jaw.

BRIEF DESCRIPTION OF THE DRAWINGS

In the accompanying drawings, structures are illustrated that, together with the detailed description. provided below, describe exemplary embodiments of the claimed invention.

In the drawings and description that follows, like elements are identified with the same reference numerals.

DETAILED DESCRIPTION

Figure 1:
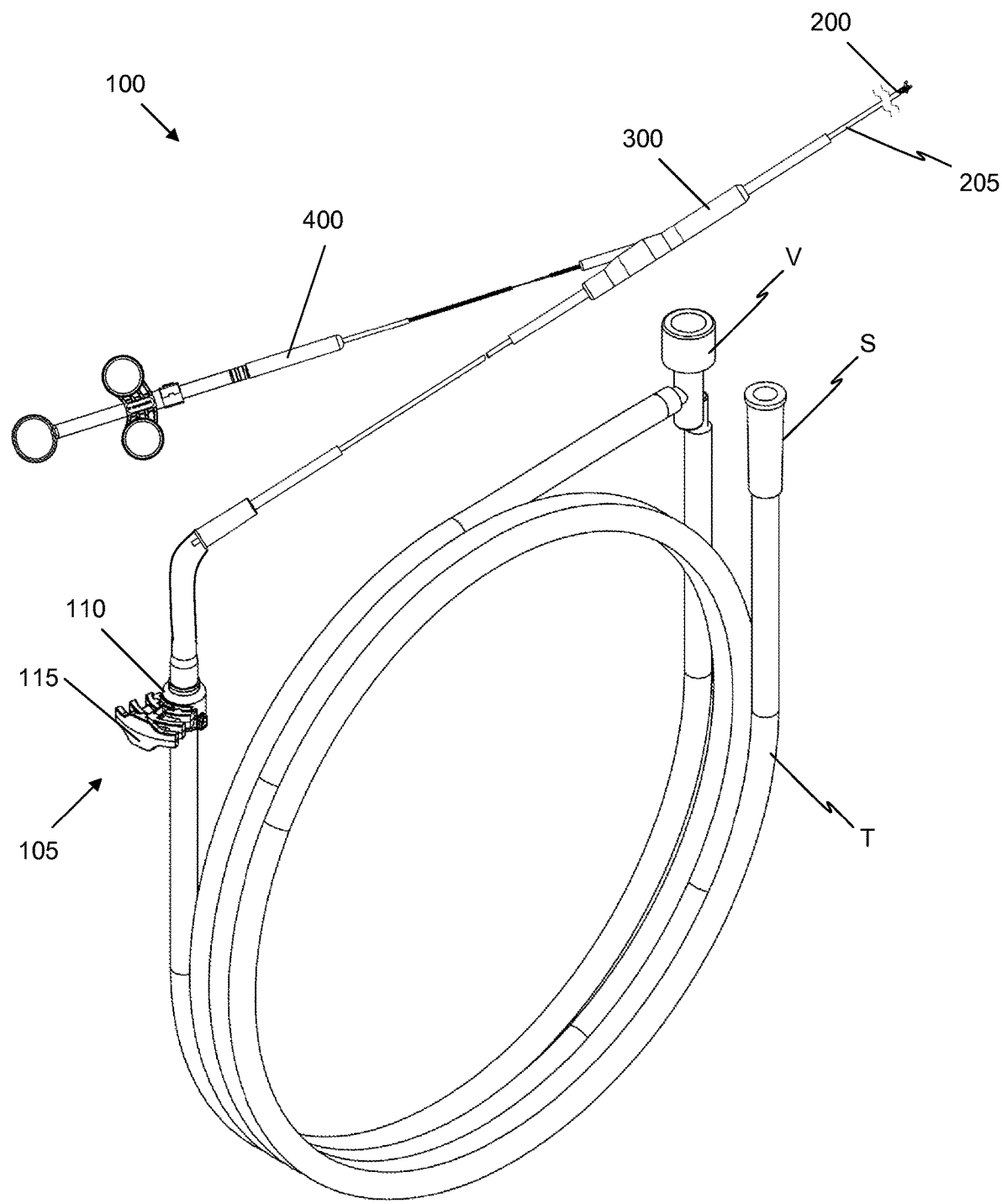
FIG. 1 is a perspective view of one embodiment of an endoscopic biopsy assembly.

FIG. 1 is a perspective view of one embodiment of an endoscopic biopsy assembly 100. The endoscopic biopsy assembly 100 is for use with an endoscope (not shown) and includes a biopsy forceps device 200 disposed therein. The endoscope may be any known endoscope. In one known embodiment, the endoscope is an Olympus 160-series endoscope.

A catheter 205 is operatively connected to the biopsy forceps device 200, and passes through the endoscope and a connector 300, to a sample collection chamber 105. In the illustrated embodiment, the collection chamber includes a tube 110, having an aperture for receiving a tray 115 with a handle. The tray 115 may be slidably removed from the aperture. In one embodiment, the tray 115 may be held in place by a locking mechanism (not shown). Such a locking mechanism may include a pivoting or flexible member and a projection that is received in an aperture of the handle of the tray 115.

In the illustrated embodiment, the tray 115 has a single sample receiving surface. In an alternative embodiment (not shown), the tray includes one or more dividers that define a plurality of sample receiving surfaces. The dividers may be walls that extend upwards from a bottom surface of the tray, or the dividers may be indentations formed in the bottom surface of the tray. Such a tray may be moved within the sample collection chamber 105, such as by sliding, pivoting, or rotating, to receive samples on the different sample receiving surfaces.

Alternatively, the sample collection chamber 105 may be any existing collection chamber. In one known embodiment (not shown), the sample collection chamber 105 is a polypectomy trap adapter commercially available under the name ETRAP polyp trap and sold by U.S. Endoscopy. The sample collection chamber 105 may include multiple components constructed of polymeric materials, such as thermoplastic elastomers or clear rigid plastic.

An actuation handle 400 is also operatively connected to the biopsy forceps device 200 through connector 300. As will be described in further detail below, the actuation handle 400 includes a sliding member and a shaft. The sliding member may be manually translated along the shall, which causes the biopsy forceps device 200 to open and close. The actuation handle 400 may be constructed of metal or a polymeric material, such as acrylonitrile butadiene styrene ("ABS") plastic.

In the illustrated embodiment, the sample collection chamber 105, connector 300, and actuation handle 400 are spaced from each other. In alternative embodiments (not shown) one or more of the sample collection chamber 105, connector 300 and actuation handle 400 may be directly attached to each other. Such attachments may be permanent attachments or releasable attachments. For example, in one embodiment (not shown), the sample collection chamber 105 is fixedly or releasably attached to the actuation handle 400. In another embodiment (not shown), the sample collection chamber 105 is releasably attached to the connector 300. In yet another embodiment, the connector 300 is releasably attached to the actuation handle 400. Releasable attachments may be formed by clips, VELCRO, snaps, threaded connectors, or other known releasable connectors. Fixed attachments may be formed by adhesive, bolts, rivets, welds, and other known fixed connectors. A fixed attachment may also be formed by molding two or more components as a single component.

In the illustrated embodiment, a suction device (not shown) is connected to a suction end S of a tube T, and the tube T is operatively connected to the sample collection chamber 105. A valve V is disposed along tube T. When the suction device is turned on and the valve V is open, suction is applied through the tube T, and through the sample collection chamber 105 and catheter 205 to the distal end of the biopsy forceps device 200. The tray 115 in the sample collection chamber 105 includes a plurality of apertures, so as not to interrupt suction along the tube T to the biopsy forceps device 200. When the suction device is turned on and the valve V is closed, suction is only applied through a portion of the tube T.

In the illustrated embodiment, the valve V is biased in a closed position and is opened by a manually operated push button. In the illustrated embodiment, the valve is a trumpet valve. In an alternative embodiment (not shown), the valve is opened by a foot pump or a clamp. In another alternative embodiment (not shown) the valve is disposed on the sample collection chamber 105 or the catheter 205.

In operation, the operator guides the endoscope to the biopsy site while viewing the biopsy site through various optical features allowing for visualization. The operator positions the biopsy forceps device 200 at a desired location and actuates the actuation handle 400 to open the biopsy forceps device 200. The operator optionally applies suction through the biopsy forceps device 200 by opening the valve V. Applying suction at this time may cause "tenting" of the tissue, thus facilitating the taking of a sample. The operator then actuates the actuation handle 400 to close the biopsy forceps device 200 around a tissue sample. The act of closing the biopsy forceps device 200 may sever the tissue sample in some instances. In other instances, the operator may need to apply force to withdraw the biopsy forceps device 200 from the biopsy site. This additional force may help to sever the tissue sample from the site. After the sample has been severed, if the valve V has not been previously opened, the operator opens the valve V to apply suction. The suction evacuates the sample from the biopsy forceps device 200 and draws it through the catheter 205 to the sample collection chamber 105. The valve V may be opened before or after the actuation handle 400 is actuated.

The endoscopic biopsy assembly 100 may be operated by one or more operators. For example, a first operator may guide the endoscope, a second operator may actuate the actuation handle 400, a third operator may open and close the valve V, and a fourth operator may retrieve the tissue sample from the sample collection chamber 105. Alternatively, a single operator may perform each of these tasks. As another alternative, two or three operators may operate the endoscopic biopsy assembly 100, with each operator performing one or more tasks.

Figure 2B:
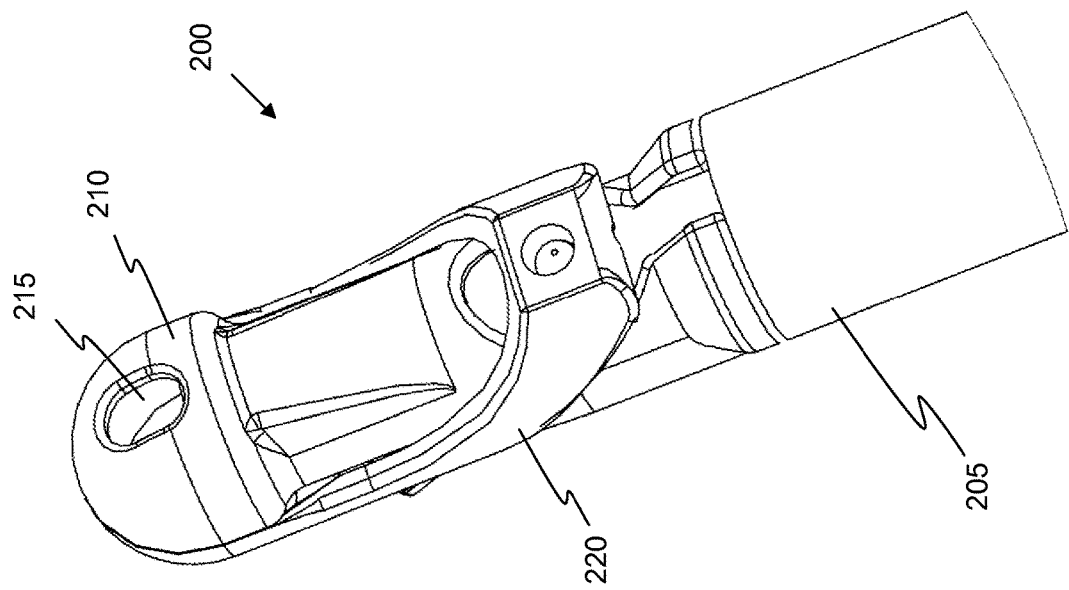
FIG. 2B is a second perspective view of the distal end of the biopsy forceps device, showing jaws in a closed position.
Figure 2A:
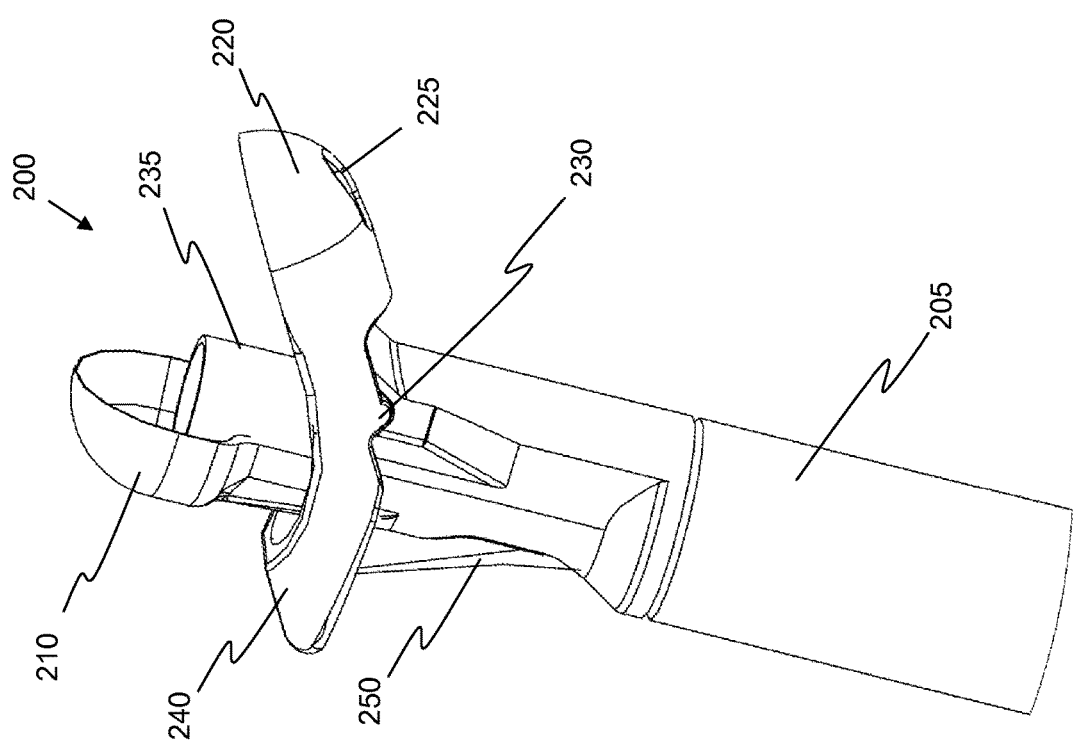
FIG. 2A is a first perspective view of a distal end of one embodiment of a biopsy forceps device of the endoscopic biopsy assembly, showing jaws in an open position.

FIGS. 2A and 2B illustrate first and second perspective views of the biopsy forceps device 200 connected to a catheter 205. The biopsy forceps device 200 includes a stationary jaw 210 having fenestration 215 and movable jaw 220 also having fenestration 225. In alternative embodiments (not shown), the stationary jaw 210, movable jaw 220, or both are solid and do not include fenestrations. In another alternative embodiment (not shown), but jaws are movable.

Figure 2D:
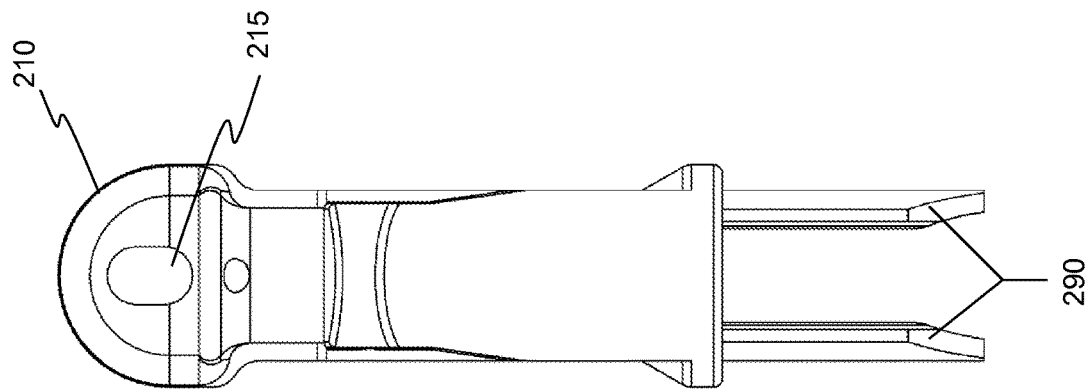
FIG. 2D is a top plan view of one embodiment of a stationary jaw of the biopsy forceps device.
Figure 2C:
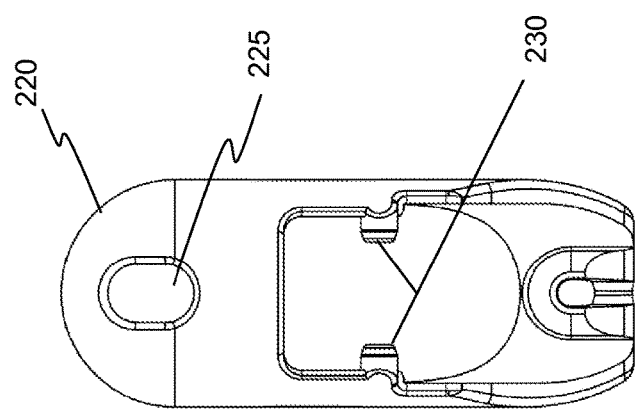
FIG. 2C is a top plan view of one embodiment of a movable jaw of the biopsy forceps device.

FIGS. 2C and 2D illustrate top plan views of the movable jaw 220 and the stationary jaw 210. Referring now to FIGS. 2A-D, each of the stationary jaw 210 and movable jaw 220 have sharpened edges configured to cut tissue. The sharpened edges may be continuous edges or serrated edges. In the illustrated embodiment, each of the stationary jaw 210 and movable jaw 220 have a radial curve and are cup shaped. In alternative embodiments (not shown), the jaws may have non-radial curves, or straight edges that form a geometric shape.

Each of the stationary jaw 210 and movable jaw 220 may be formed by a metal injection molding ("MIM") or other processes including, but not limited to, stamping, laser welding, sintering, and molding. The jaws may be constructed of stainless steel, aluminum, titanium, ceramics, plastics, or other known materials.

The catheter 205 may be constructed of a polymeric material, such as TEFLON, polyethylene, polypropylene, nylon, polyetherether keytone (PEEK), and other polymeric materials. The catheter 205 may be formed by an extrusion process.

The movable jaw 220 is connected to the stationary jaw 210 by a pivot 230. In the illustrated embodiment, the pivot 230 includes two posts that extend from the movable jaw 220 and are seated in corresponding apertures of the stationary jaw 210. In an alternative embodiment (not shown), the pivot 230 includes two posts that extend from the stationary jaw 210 and are seated in corresponding apertures of the movable jaw 220. In another alternative embodiment (not shown), both the stationary jaw 210 and the movable jaw 220 include a pair of corresponding apertures, and a pin is inserted therein to form a pivot. In each such embodiment, the pivot may be positioned so as not to interfere with a passageway for tissue samples. In such embodiments, the pivot may be described as an external pivot. Alternatively, the pivot may cross such a passageway.

The biopsy forceps device 200 further includes suction tubing 235 having a first end disposed within the chamber formed by stationary jaw 210 and movable jaw 220. In the illustrated embodiment, the end of the suction tubing 235 is positioned forward of the pivot 230, such that when the movable jaw 220 is opened, the first end of the suction tubing 235 may directly contact tissue. An operator may choose to apply suction prior to taking a tissue sample, such that when the valve V is open and suction is applied through the suction tubing 235, the tissue that is in direct contact with the suction tubing 235 is raised. This may be referred to as "tenting." The tenting process pulls tissue between the jaws, so that when the movable jaw 220 is closed, the sharpened edges of the jaws may sever the tented tissue and capture a sample between the jaws. An additional backwards force may also be required to sever the tissue sample. The tissue sample is subsequently drawn down the catheter by the applied suction.

In one embodiment, the suction tubing 235 is an insert that extends partially into the catheter. In an alternative embodiment, the suction tubing 235 extends the length of the catheter.

The movable jaw 220 further includes a lever arm 240 having an aperture 245. A wire 250 engages the lever arm 240 through the aperture 245, such that manipulation of the wire 250 moves the lever arm 240 about the pivot 230, causing the movable jaw 220 to open and close. The wire 250 may be manipulated through the actuation handle 400.

Figure 3:
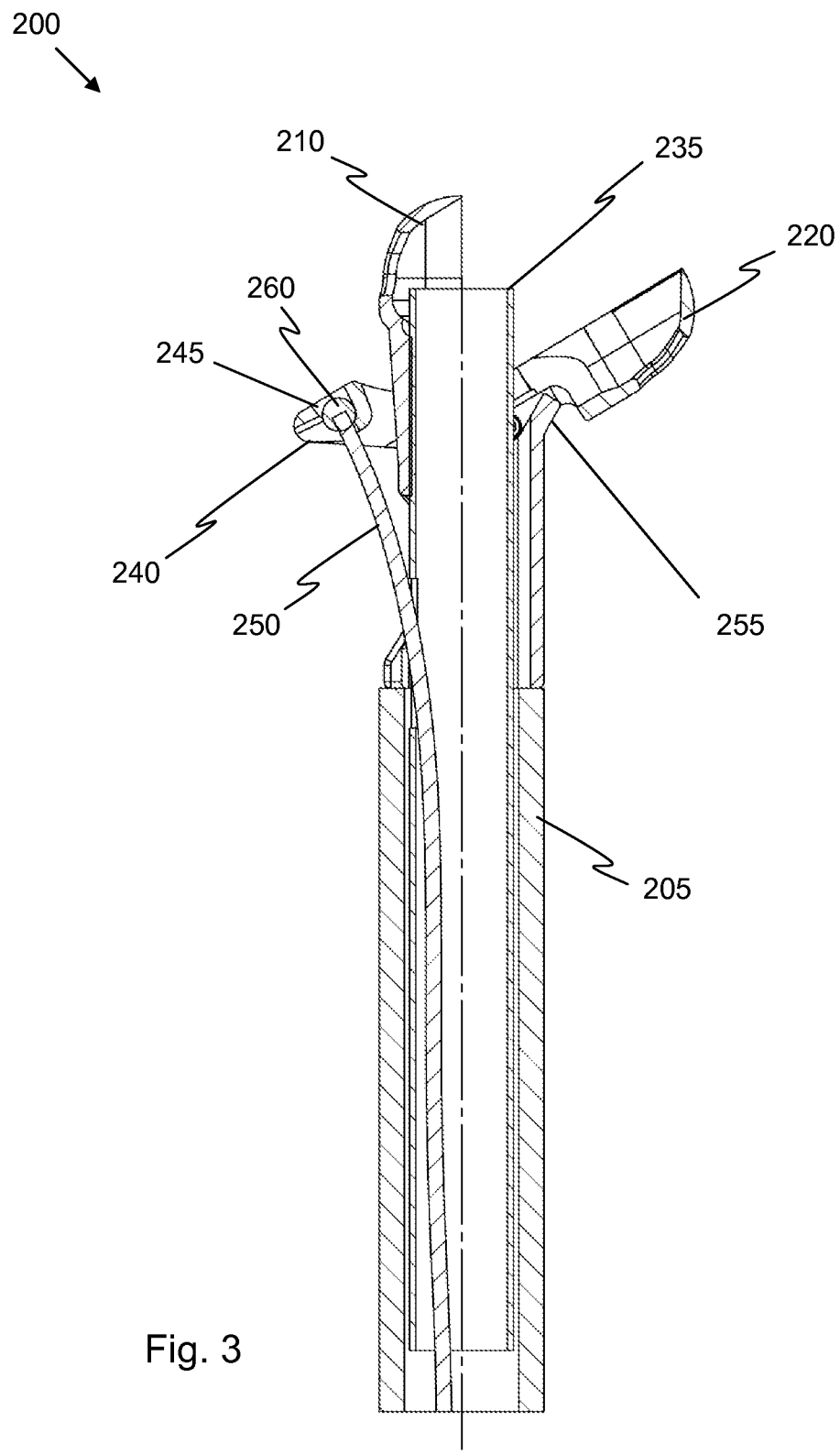
FIG. 3 is a cross-section of the distal end of the biopsy forceps device.

FIG. 3 illustrates a cross-section of the biopsy forceps device 200. As can be seen in this view, the stationary jaw 210 further includes a ledge 255 disposed opposite the cutting surface of the stationary jaw 210. The ledge 255 may be created during the manufacturing process to form apertures in the stationary jaw 210 to accept the posts of the movable jaw 220. In one embodiment, a staking operation is performed to bend the ledge 255. In the illustrated embodiment, the ledge 255 forms a stop, thereby defining the arc through which the movable jaw 220 may pivot. Alternatively, the ledge 255 may be dimensioned so as not to interfere with the pivoting of the movable jaw 220.

With continued reference to FIG. 3, the aperture 245 in the lever arm 240 forms a socket that engages a ball 260 at the end of the wire 250. During the manufacturing process, the outer edges of the aperture 245 may be crimped or otherwise closed around the ball 260 after the wire is received, such that the ball will remain housed in the socket formed by aperture 245 during operation of the endoscopic biopsy assembly 100. In one embodiment, a staking operation is performed to secure the ball 260 in the socket. In an alternative embodiment (not shown), a stop is formed on the wire on the opposite side of the lever arm, such that the lever arm is sandwiched between the ball 260 and the stop.

In the illustrated embodiment, the distal end of the suction tubing 235 is slightly spaced from the distal end of the jaws 210, 220. In an alternative embodiment (not shown), the distal end of the suction tubing 235 may be positioned adjacent the distal end of the jaws 210, 220. In another alternative embodiment (not shown), the distal end of the suction tubing 235 may be further spaced from the distal end of the jaws 210, 220, such that the suction tubing 235 is bellow the ball 260 of the wire 250. In one known embodiment, the position of the suction tubing 235 may be varied before or during an operation.

Figure 4:
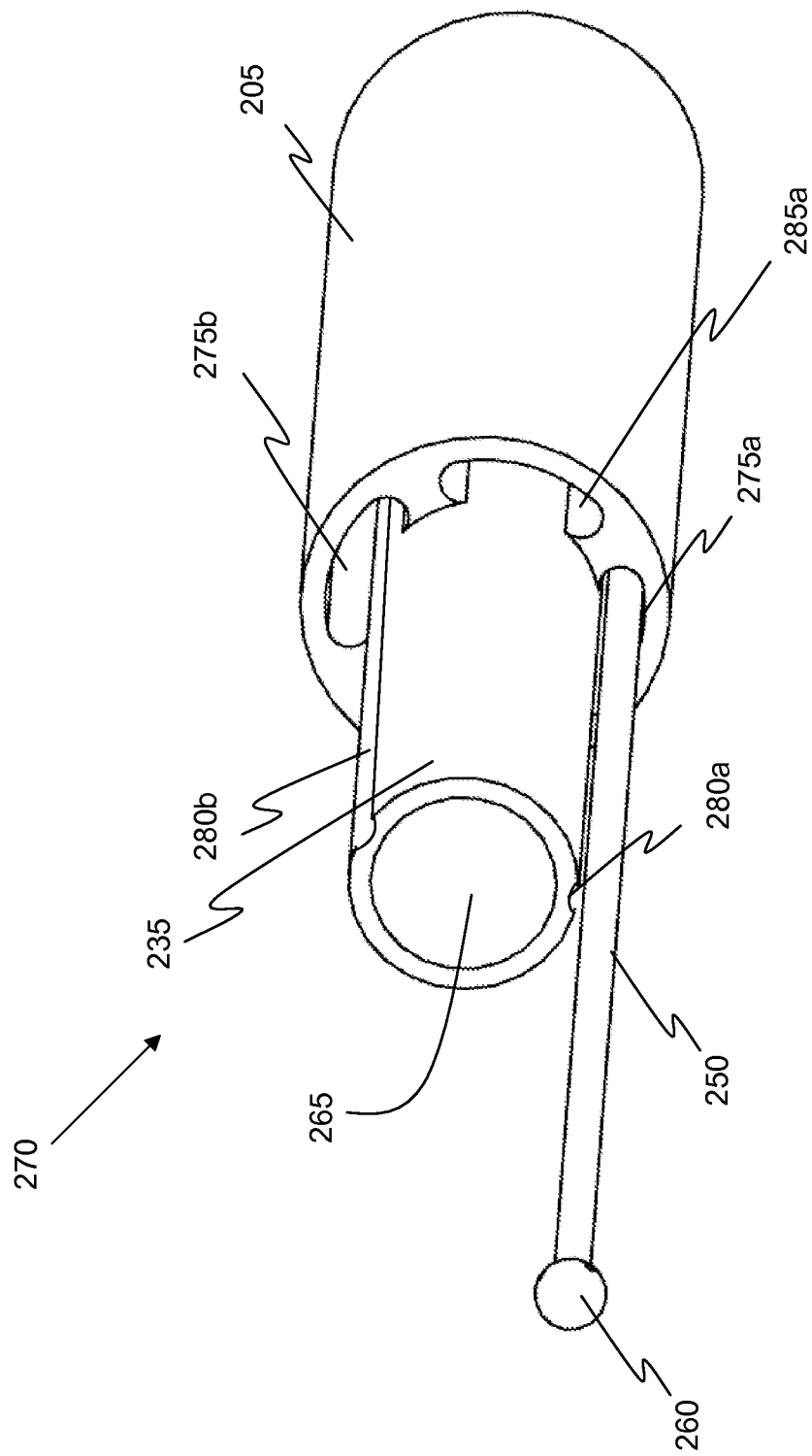
FIG. 4 is a partial perspective view of one embodiment of a catheter and wire assembly of the endoscopic biopsy assembly.

FIG. 4 illustrates a partial perspective view of one embodiment of a catheter assembly 270. In this embodiment, the catheter assembly includes the catheter 205 and suction tubing 235. The suction tubing 235 may be a separate component or it may be integral with the catheter 205. The catheter 205 may be constructed of a polymeric material such as polytetrafluoroethylene ("PTFE"). The suction 235 tubing may also be constructed of a polymeric material such as PTFE.

The center of the suction tubing 235 is a hollow passageway 265 through which tissue samples may be drawn. The hollow passageway 265 is operatively connected to the suction device, such that when the suction device is turned on and the valve V is open, suction will be applied to the passageway 265 and draws a severed tissue sample to the capture container 105.

In the illustrated embodiment, the catheter 205 further includes a pair of lumens 275a,b configured to receive the wire 250. Although only one of the lumens (275a) is used, two lumens are formed for manufacturing purposes. Additionally, a pair of corresponding grooves 280a,b are formed on the suction tubing 235. The grooves 280a,b may extend the entire length of the suction tubing 235, or may only extend along a portion of the suction tubing 235. The corresponding grooves 280a,b are aligned with the lumens 275a,b and may restrict lateral movement of the wire 250. The inclusion of a lumen 275 for the wire 250 that is separate from the passageway 235 ensures that the tissue sample has a clear travel path to the collection chamber 105. However, it should be understood that the lumen 275 is optional and that the wire ay be disposed along the passageway 235.

Additionally, the catheter 205 includes a pair of notches 285a,b or other apertures configured to receive tangs 290 of the stationary jaw 210 (as shown in FIG. 2D). The notches 285a,b may extend for a portion of the catheter 205, or they may extend the entire length of the catheter 205. During assembly of the biopsy forceps device 200, adhesive may be placed in the notches 285a,b such that the jaws are thereby affixed to the catheter 205. Where adhesive is to be used, the surface may be scored to aid in bonding. The notches 285a,b serve as an anchor point for the base of the stationary jaw 210 and prevents the jaws from rotating relative to the catheter.

In an alternative embodiment (not shown), the notches 285a,b are replaced with an annular groove configured to receive a flange of the jaws. In another alternative embodiment (not shown), the catheter does not include notches or a groove, and the jaws are glued, welded, or otherwise affixed to the catheter.

Figure 5:
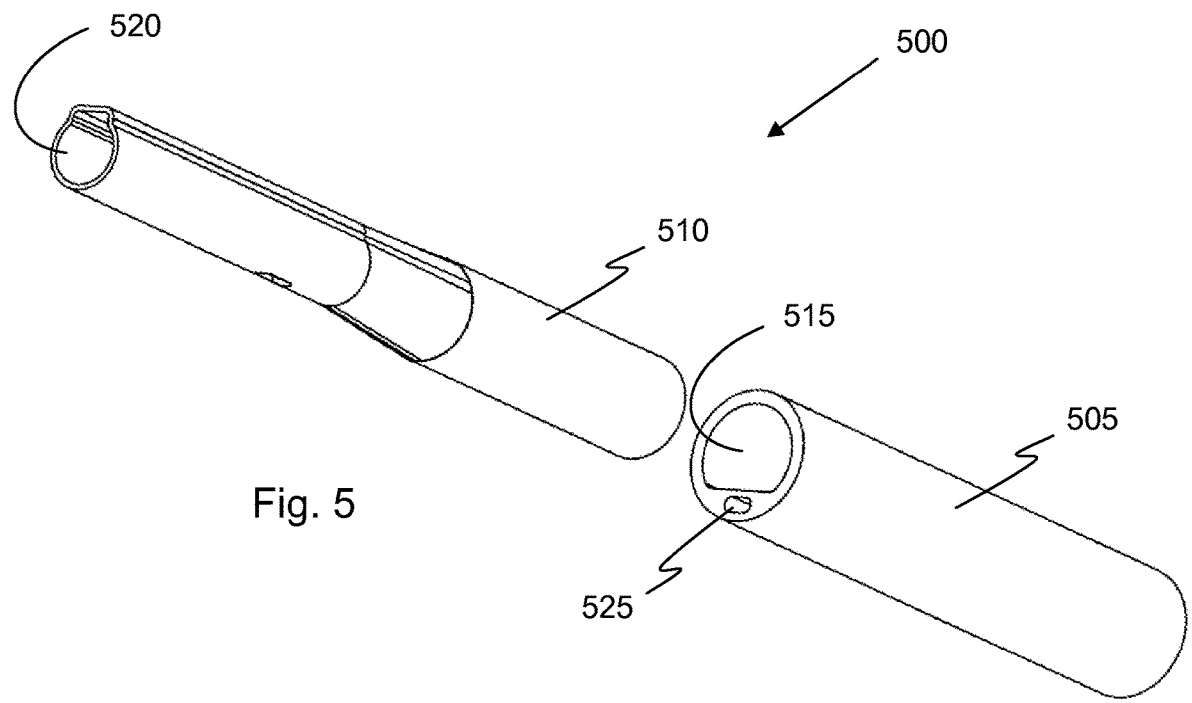
FIG. 5 is a perspective view of an alternative embodiment of a catheter assembly of the endoscopic biopsy assembly.

FIG. 5 illustrates a perspective view of an alternative embodiment of a catheter assembly 500. In this embodiment, the catheter assembly includes the catheter 505 and suction tubing 510, wherein the suction tubing 510 is a separate insert that is received in a hollow passageway 515 of the catheter 505. The center of the suction tubing 510 is also a hollow passageway 520 for tissue samples.

In the illustrated embodiment, the catheter 505 further includes a lumen 525 configured to receive a wire. The inclusion of a lumen 525 for the wire ensures that the tissue sample has a clear travel path to the collection chamber 105.

Figure 6:
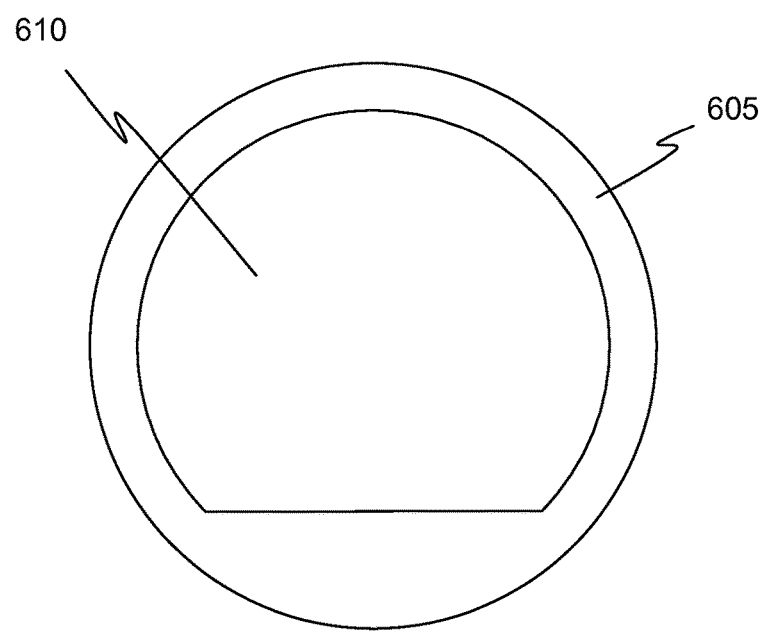
FIG. 6 is a front view of another alternative embodiment of a catheter of the endoscopic biopsy assembly.

FIG. 6 illustrates a front view of an alternative embodiment of a catheter Catheter 605 may be employed in catheter assembly 270 or 500, or other variations. The catheter 605 includes a hollow passageway 610. The catheter 605 does not include any lumens for a wire. Instead, the wire may be disposed along the passageway 610.

Figure 7:
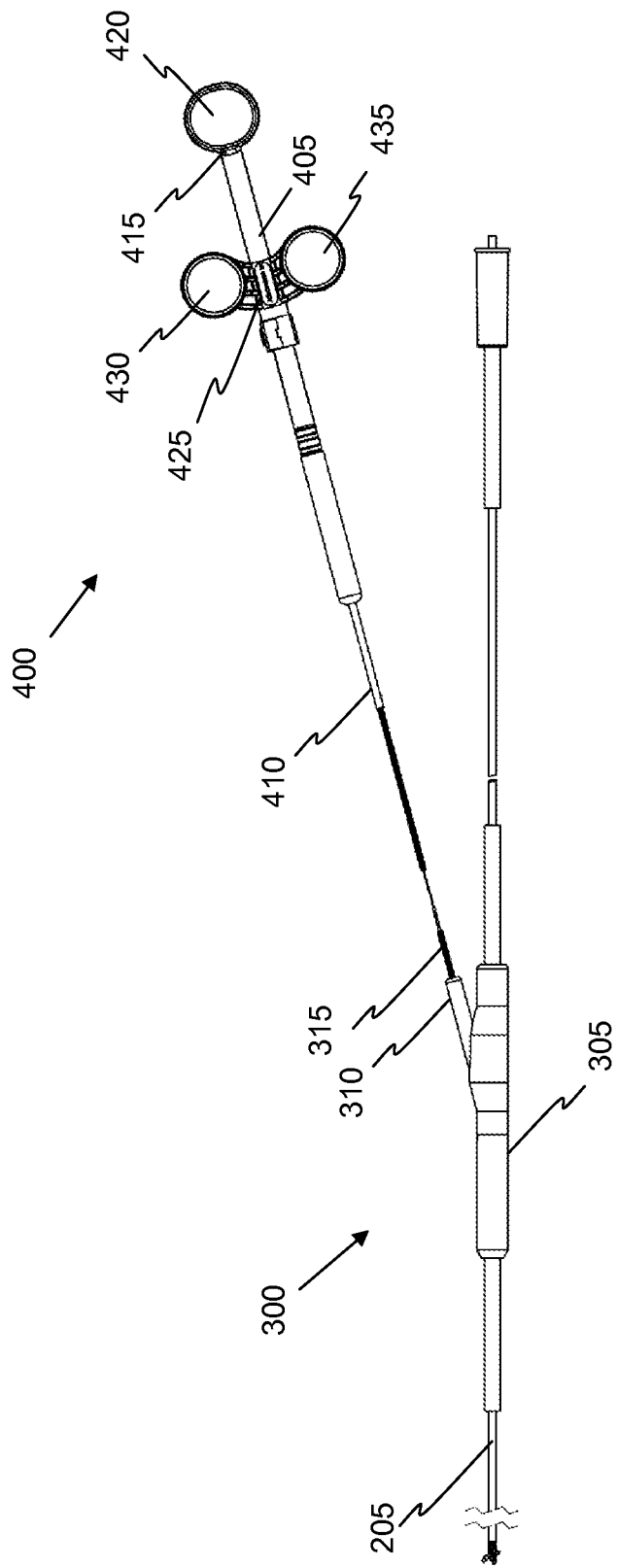
FIG. 7 is a side view of one embodiment of a connector and actuation handle of the endoscopic biopsy assembly.

FIG. 7 illustrates a side view of one embodiment of a connector 300 and actuation handle 400 of the endoscopic biopsy assembly 100. The connector 300 is a substantially "y-shaped" component, having a major chamber 305 and a minor chamber 310. The catheter 205 passes through the major chamber 305 to the sample collection chamber 105. A cable 315 leads from the minor chamber 310 to the actuation handle 400.

The actuation handle 400 includes a shaft 405 having a distal end 410 and a proximal end 415. In the illustrated embodiment, the proximal end 415 has a first ring 420 attached thereto. The first ring 420 is configured to receive an operator's thumb or finger. However, it should be understood that the ring may be omitted or replaced with a transversely oriented member.

A sliding member 425 is slidably mounted to the shaft 405. In the illustrated embodiment, the sliding member 425 includes a second ring 430 and a third ring 435, each configured to receive an operator's finger or thumb. Alternatively, the sliding member 425 may be a spool, or include a transversely oriented member in lieu of rings.

A proximal end of the wire 250 is fixedly attached to the sliding member 425. When the sliding member is translated towards the proximal end 415 of the shaft 405, the wire 250 is retracted. This retraction causes the ball 260 at the opposite end of the wire 250 to pull the lever arm 240 of the movable jaw 220, which causes the movable jaw 220 to pivot towards the closed position. Likewise, when the sliding member is translated towards the distal end 410 of the shaft 405, the wire 250 is pushed forward. This movement causes the ball 260 at the opposite end of the wire 250 to push the lever arm 240 of the movable jaw 220, which causes the movable jaw 220 to pivot towards the open position.

Figure 8:
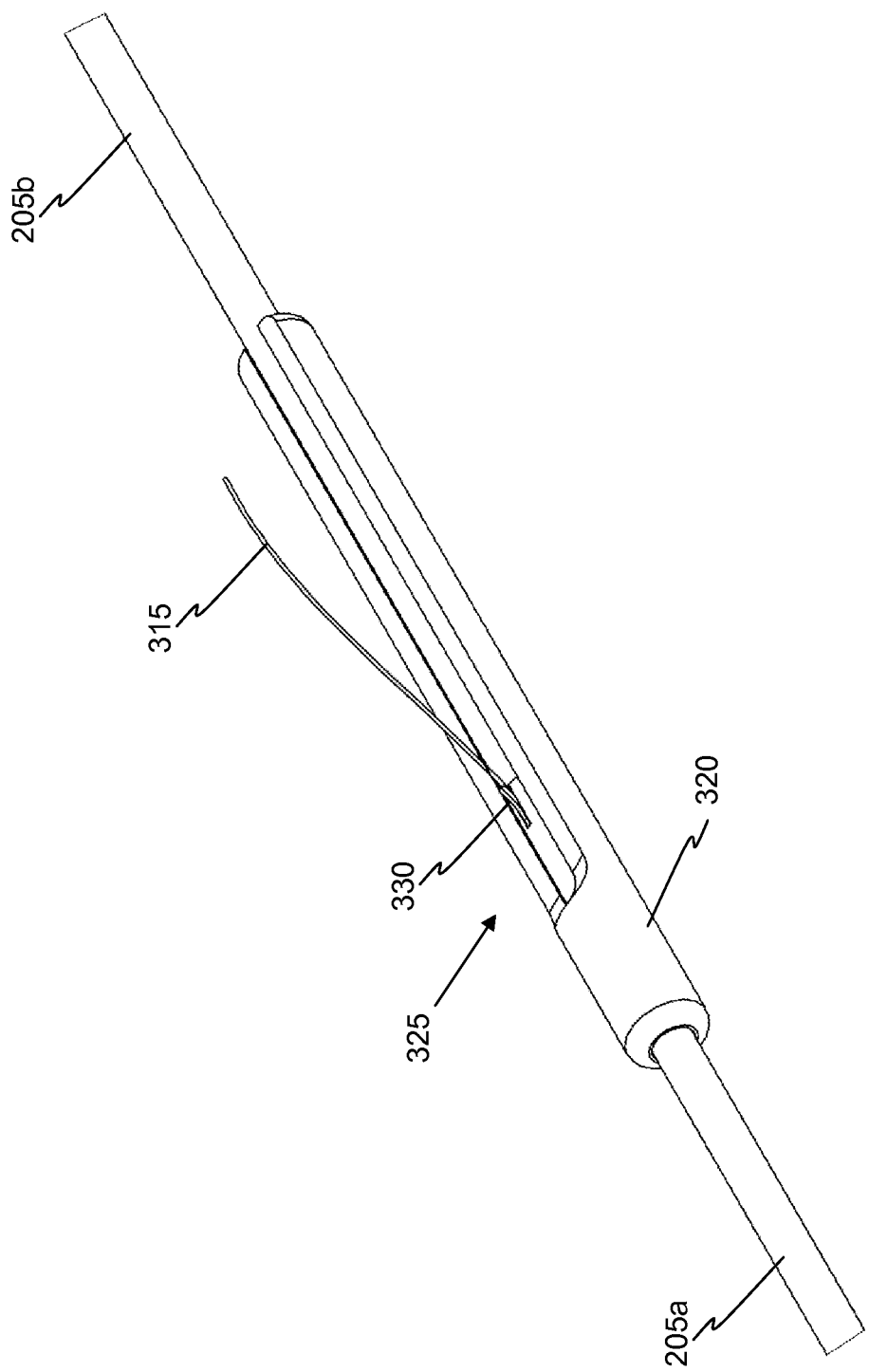
FIG. 8 is a perspective view of assembled connecting components configured to be housed in the connector.

FIG. 8 illustrates a perspective view of assembled connecting components disposed within the connector 300. In this embodiment, the catheter 205 connected to the biopsy forceps device 200 includes a first catheter 205a and a second catheter 205b. End portions of each of the first and second catheters 205a,b are disposed in an aligning member 320. The aligning member 320 is a hollow rod having an elongated cavity to receive the first and second catheters 205a,b. The aligning member 320 further includes a side opening 325. In the illustrated embodiment, the side opening 325 is formed by a chamfer extending downwards to the cavity and outwards to an end of the aligning member 320. In an alternative embodiment (not shown), the side opening may extend the entire length of the aligning member 320. In another alternative embodiment (not shown), the side opening may be a hole or slot that does not extend to an end of the aligning member 320.

The connecting components may be assembled in the following manner. A first end of the first catheter 205a is inserted into a first end of the aligning member 320. The first catheter 205a may be affixed in its position with adhesive, or by a press fit. The first end of the first catheter 205a includes a notch 330 that provides an exit for the cable 315. The first catheter 205a is positioned such that the notch 330 and the cable 315 are accessible through the side opening 325 of the aligning member 320. In the illustrated embodiment, a flap of the catheter remains in place over the notch 330. This flap may shield the wire from adhesive that is applied during assembly.

A first end of the second catheter 205b is then inserted into a second end of the aligning member 320, such that it abuts the first end of the first catheter 205a. The second catheter 205b may be affixed in its position with an adhesive or by a press fit.

Figure 9:
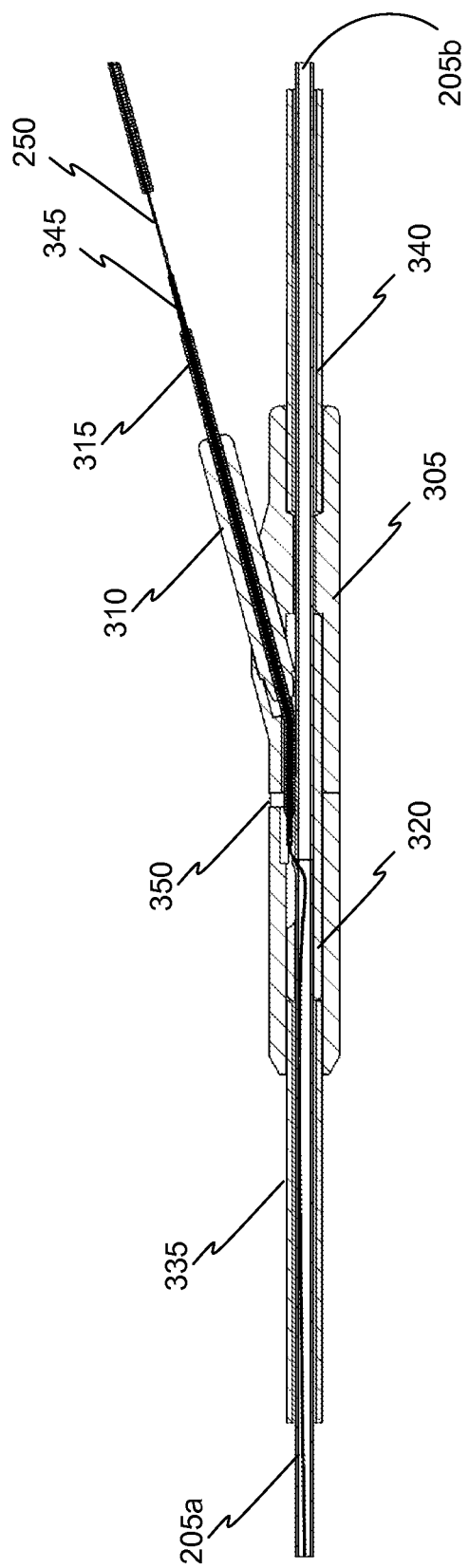
FIG. 9 is a cross-section of the connector of the endoscopic biopsy assembly.

FIG. 9 illustrates a cross-section of the connector 300. As explained above, the first and second catheters 205a,b pass through the major chamber 305 of the connector 300. A first outer tube 335 surrounds the catheter 205 at a front end of the major chamber 305, forward from the aligning member 320. A second outer tube 340 surrounds the catheter 205 at a rear end of the major chamber 305. The first and second outer tubes 335, 340 may prevent crimping or strains on the catheter 205 near the connector 300. In an alternative embodiment (not shown), a single outer tube may extend through the entire connector 300. In another alternative embodiment (not shown), no outer tubes are included.

As further explained above, a cable 315 extends from the minor chamber 310. A portion of the cable 315 is shown in cutaway for illustrative purposes. The cable 315 may be a sheath spring having tubing 345 disposed therein. In one embodiment, the tubing 345 is PEEK tubing. The wire 250 is disposed within the cable 315. The wire 250 extends from the sliding member 425 of the actuation handle 400, through the cable 315 and the minor chamber 310, and joins the catheter 205 inside the major chamber 305 of the connector 300. The wire 250 either extends through a lumen or the hollow passageway in the catheter 205. The cable 315 may act as a dampener that prevents the sliding member 425 of the actuation handle 400 from being translated too quickly or violently.

In the illustrated embodiment, the minor chamber 310 extends from the major chamber 305 at an angle of approximately 15°. In alternative embodiment, the minor chamber 310 may extend from the major chamber at an angle between 5° and 60°. A smaller angle may be preferable to prevent crimping of the wire 250.

In the illustrated embodiment, the major chamber 305 also includes a sterilization hole 350. The sterilization hole 350 is configured to receive sterilizing material, such as ethylene oxide, as may be needed or desired.

Figure 10:
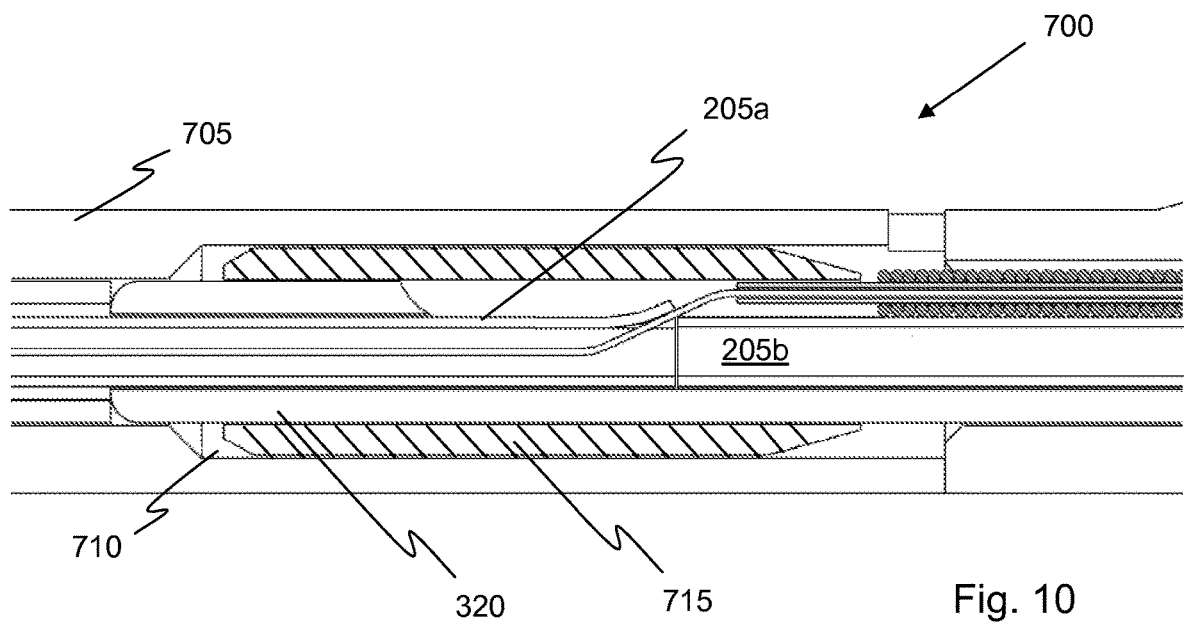
FIG. 10 is a cross-section of an alternative embodiment of a connector of an endoscopic biopsy assembly.

FIG. 10 illustrates a partial cross-section of an alternative embodiment of a connector 700 of an endoscopic biopsy assembly. The connector 700 is substantially the same as the connector 300, except for the differences described herein. Like reference numbers indicate like components. The connector 700 includes a major chamber 705 having an enlarged cavity portion 710 sized to accept a housing 715. The housing 715 surrounds portions of the aligning member 320, the first catheter 205a, and the second catheter 205b.

Figure 11:
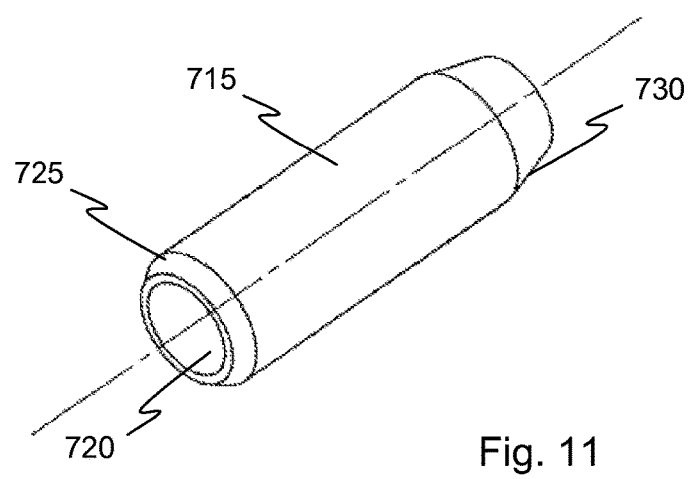
FIG. 11 is a perspective view of one embodiment of a housing in the alternative embodiment of the connector.

FIG. 11 illustrates a perspective view of the housing 715. The housing 715 has a through hole 720 and tapered ends 725, 730, and may form a seal around the enclosed components. As best shown FIG. 10, a distal end of the housing 715 surrounds a cylindrical distal end of aligning member 320 to create a seal therewith. If desired, small gaps or clearances can be filled with adhesive, grease, sealing compounds and the like to create an air-tight seal. A proximal end of aligning member 320 includes the side opening 325 (see FIG. 8). The side opening 325 creates a gap between housing 715 and second catheter 205b for the passage of an "S" portion of cable 315. While not shown, the gap may be filled around the cable 315 with a seal 316 such as elastomeric seal or adhesive. The cable 315 may also be lubricated to prevent sticking with the seal 316. In an alternative embodiment (not shown), the ends of the housing are straight.

The housing 715 may be constructed of a polymeric material such as but not limited to ABS or any one of a number of metals. In one embodiment, the housing 715 is constructed at least partially of rubber to aid in sealing the enclosed components. In an alternative embodiment (not shown), o-rings or other seals may be disposed within the housing.

Figure 12:
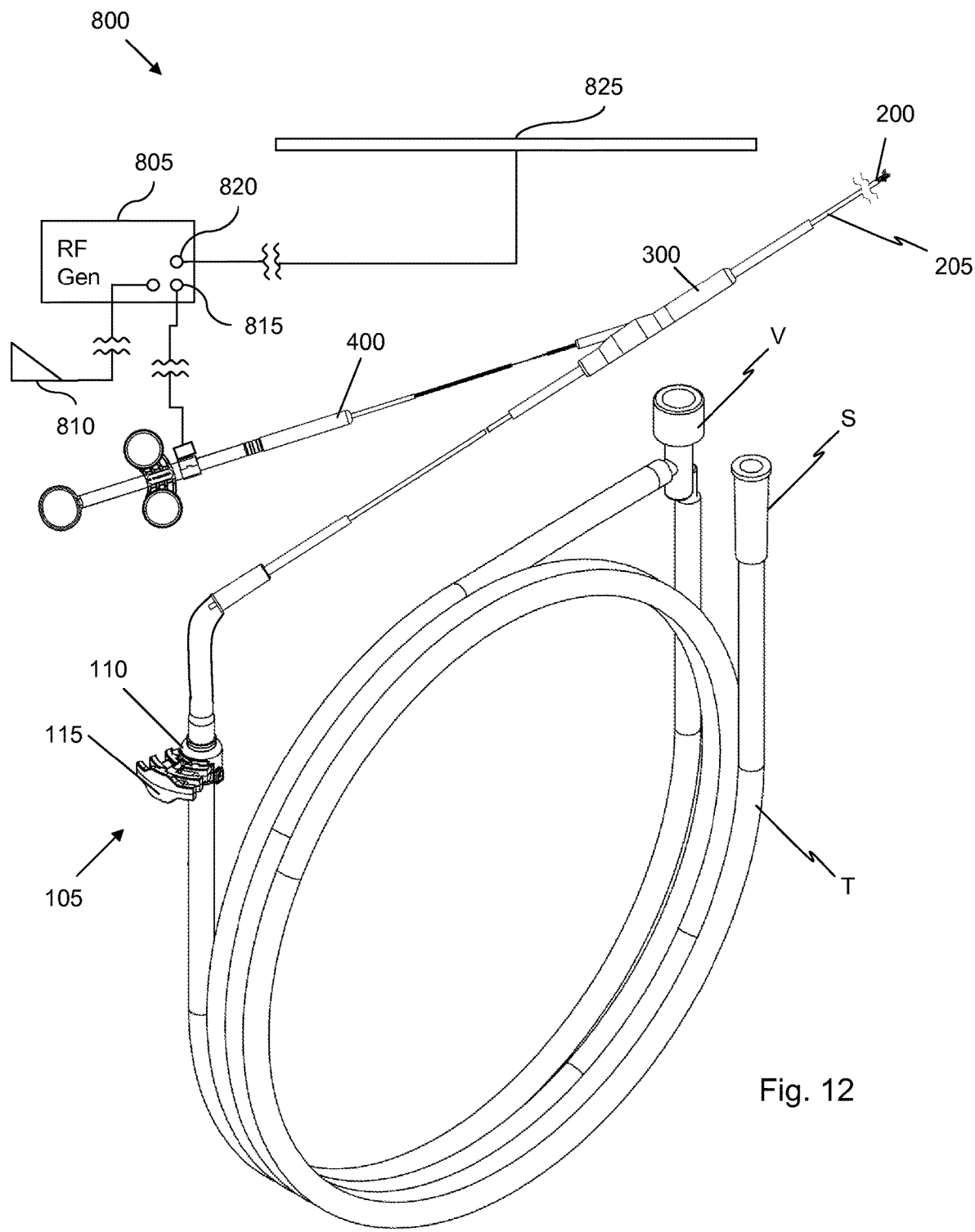
FIG. 12 is a perspective view of an alternative embodiment of an endoscopic biopsy assembly.

FIG. 12 illustrates a perspective view of an alternative embodiment of an endoscopic biopsy assembly 800. The endoscopic biopsy assembly 800 is substantially the same as the endoscopic biopsy assembly 100 shown in FIG. 1, except for the differences described herein. Like reference numbers indicate like components.

The endoscopic biopsy assembly 800 includes a radio frequency (RF) generator 805 connected to the actuation handle 400. In this embodiment, at least one of the jaws 210, 220 is formed from an electrically conductive material, such as stainless steel, and the RF generator 805 is in electrical communication with the electrically conductive jaw. In one particular embodiment, both jaws 210, 220 are formed from an electrically conductive material. In FIG. 12, handle 400 includes art RF connector socket positioned distal to a dual ring portion of the handle. The RE connector socket is electrically connected to the jaws 210, 220 via at least wire 250 for the delivery of RE energy to the jaws.

In this embodiment, the RF generator 805 is in electrical communication with at least one of the jaws 210, 220 through the wire 250. The RE generator 805 is also in electrical communication with an actuator 810 that is used by the surgeon to deliver RF energy when required. When the actuator is activated, RE energy is provided to at least one of the jaws 210, 220 that can cauterize or cut the tissue. The RF generator 805 may include a wave form selection switch (not shown) that allows an operator to select between a cauterizing waveform and a cutting waveform. In the illustrated embodiment, the actuator 810 is a foot pedal. However, it should be understood that any actuator may be employed, such as buttons, dials, and switches.

In the illustrated embodiment, the RE generator 805 has a first pole 815 (i.e., a positive pole) and a second pole 820 (i.e., a negative pole or a ground pole). In the illustrated embodiment, only the first pole 815 is in electrical communication with at least one of the jaws 210, 220, making the biopsy forceps device 200 a monopolar device. The second pole 820 is connected to a ground pad 825. The pad 825 is placed under the patient to form an electrical ground between the patient and the RE generator 805. In alternative embodiments (not shown), the second pole 820 may be in electrical communication with any conductive object that can contact or be placed proximal to a patient.

In an alternative embodiment (not shown), both positive and negative poles are in electrical communication with the jaws 210, 220, making the biopsy forceps device 200 a bipolar device. In such an embodiment, one of the first and second poles 815, 820 is in electrical communication with jaw 210 through a first wire, and the opposite pole is in electrical communication with jaw 220 through a second wire. Such an embodiment will electrically isolate each jaw 210, 220 and the first and second wires from electrical contact with the other to prevent shorting. To provide an electrical path to tissue, each electrically isolated jaw 210, 220 has an electrically conductive area exposed in the tissue clamping area, such as the horseshoe shaped sharpened edges that are shown contacted together when the jaws are fully closed. With this embodiment, when the empty jaws are fully closed, the electrical contact areas will short together, and prevent the generator from activating. When tissue is between the clamped jaws, the tissue provides electrical resistance in the flow path between the exposed sharpened edges, and the generator will actuate and coagulate the clamped tissue.

For the bipolar embodiment, each jaw 210, 220 may include additional insulation or electrically non-conductive materials or coatings. For example, portions of the jaws may be constructed of ceramic or a polymeric material. In one exemplary embodiment, but not limited thereto, each jaw can be completely ceramic coated with an insulating layer, and portions of the insulating layer can be removed (by grinding, masking or the like) at the wire contact area and at the horseshoe shaped tissue biting area. In this embodiment, electrical energy of one pole is conducted along the insulated wire, into the jaw 210 or jaw 220 at the wire contact area, and to tissue through the exposed horseshoe shaped tissue biting area. Such an embodiment may also deliver more focused energy that would not interfere with other electrical devices, such as a pacemaker in a patient.

Figure 13A:
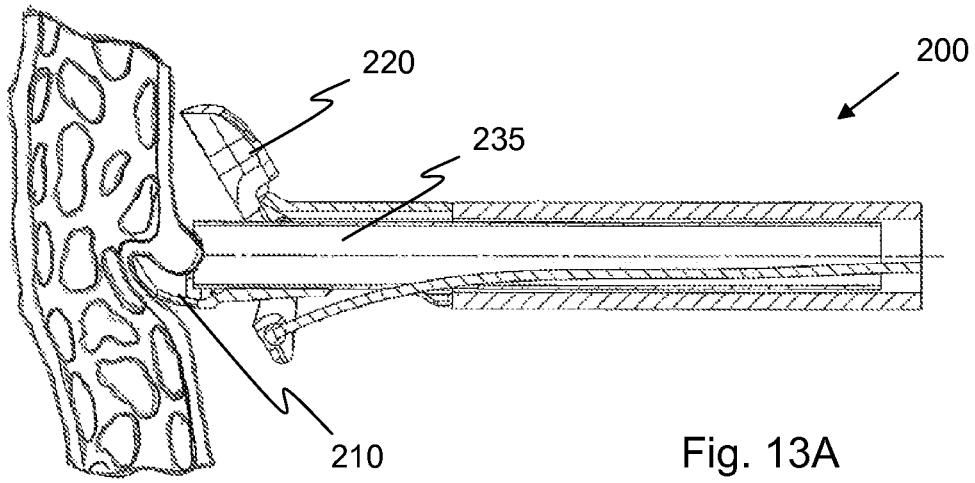
FIGS. 13A-C are cross-sections of a biopsy forceps device in the alternative embodiment of the endoscopic biopsy assembly, at various stages of taking a biopsy sample.
Figure 13B:
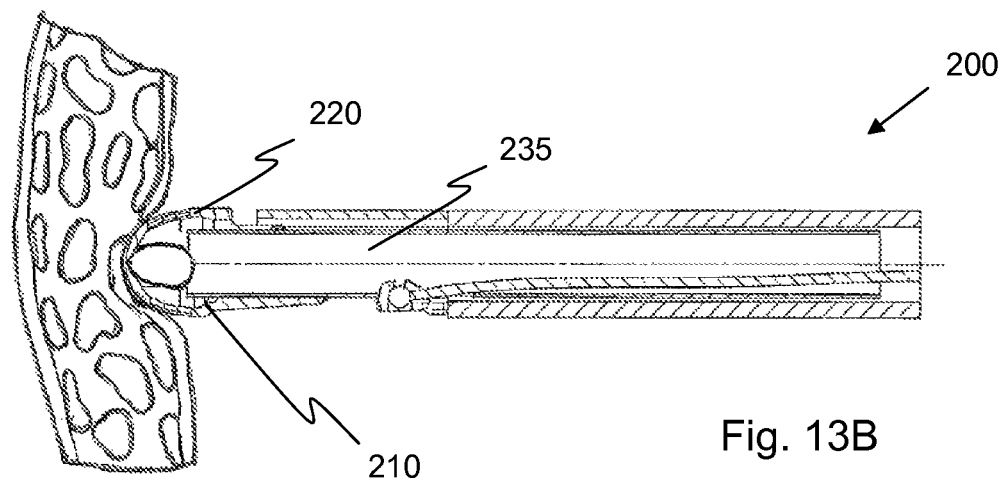
Figure 13C:
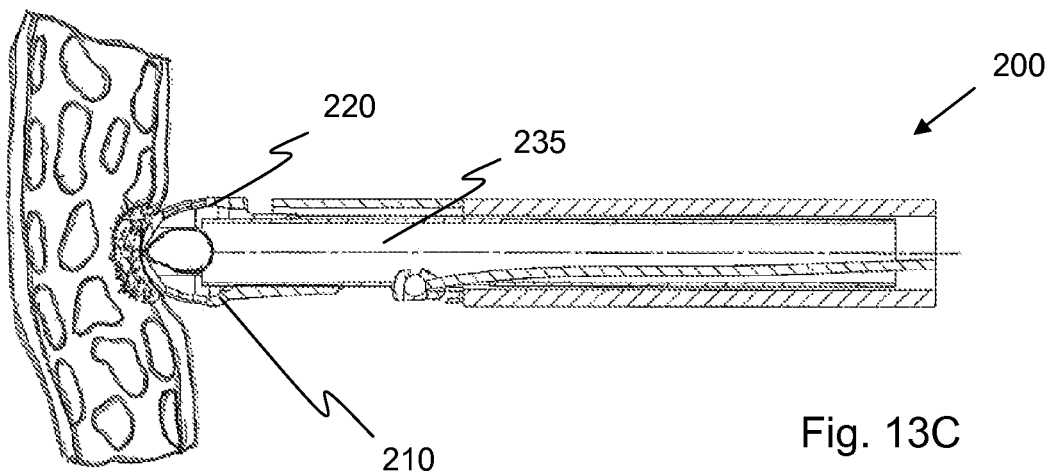

FIGS. 13A-C illustrate cross-sections of the biopsy forceps device 200 of the alternative embodiment of the endoscopic biopsy assembly 800, at various stages of taking a biopsy sample.

In FIG. 13B, the biopsy forceps device 200 has been positioned at a desired location, the jaws 210, 220 have been opened, and a potential tissue sample, such as a polyp, is shown positioned partially inside the jaws 210, 220. Once the tissue is in the jaws, suction is applied through suction tubing 235, which causes "tenting" or drawing of the tissue at least partially into the suction tubing 235 as shown. If desired, a larger bite of tissue can be taken by pushing the jaws 210, 220 farther into the tissue wall.

In FIG. 13B, the operator has actuated the actuation handle 400 to close the jaws 210, 220 of biopsy forceps device 200 around a tissue sample as it is being tented and drawn into the suction tubing 235. The act of closing the biopsy forceps device 200 pinches the "tented" tissue at the base of the polyp and in this view has fully severed the tissue sample just before it is drawn farther into the suction tubing 235 by the applied suction. In other instances, the tissue sample may not be severed entirely between the jaws 210, 220 and the operator may apply force (i.e., by pulling or shaking) to fully sever the tissue sample from the site. In still other instances, the operator may activate the RF generator to apply RF energy at the jaws to cut the tissue sample from the site. The operator may select a cutting wave form prior to activating the RIF generator.

In FIG. 13C, the closing of the jaws has failed to sever the tissue sample and, the operator is activating the RF generator to apply monopolar RF energy at the jaws to cauterize the tissue around the site. The operator may select a cauterizing wave form, such as a square wave, prior to activating the RF generator. Cauterizing the site in this manner may staunch bleeding caused by the severing, and may also kill cancer cells at the site. Because the un-severed sample is inside of the jaws, it is prevented from contacting the negatively charged patient and is not burned when the RF energy is applied. The tissue cannot be coagulated because it is exposed to only positive RF energy which travels along the external skin of the jaws and to the negatively charged patient. After applying RF energy, the operator elects to pull and shake the tissue sample free so that it can be sucked into the suction tubing 235

Figure 14:
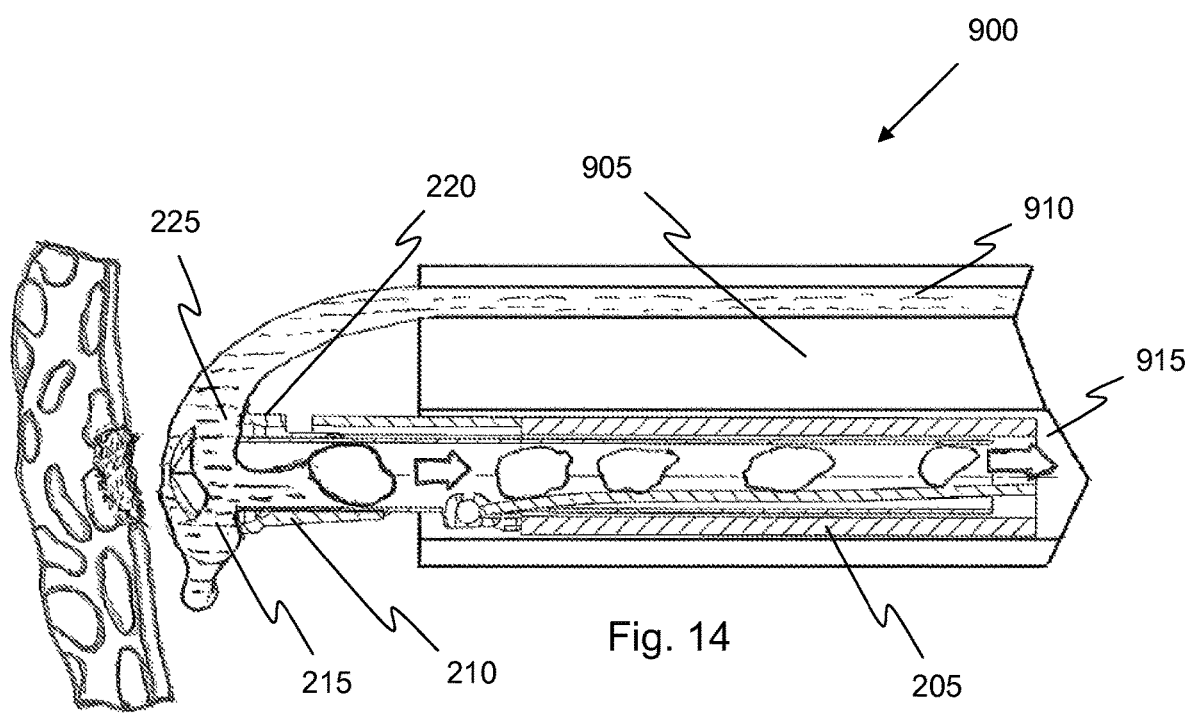
FIG. 14 is a cross-section of another alternative embodiment of a biopsy forceps device, taking a biopsy sample.

FIG. 14 illustrates a cross-section of the biopsy forceps device 200 as it extends from a distal end of an endoscope 900, while taking a biopsy sample. The biopsy forceps device 200 is the same as biopsy forceps device 200 shown in FIGS. 1-3, except for the placement within the endoscope 900. Like reference numbers indicate like components.

The endoscope 900 has a tube 905 that includes a first lumen 915 that is configured to receive the biopsy forceps device 200. Catheter 205 is shown extending along the first lumen 915 of endoscope 900 with the jaws 210, 220 extending from the endoscope 910. Endoscope 900 further comprises a second lumen 910 in communication with a fluid source for providing irrigation to tissue and to the jaws 210, 220. In the illustrated embodiment, a plurality of tissue samples have accumulated within the suction tubing 235 and the operator may irrigate the surgical site by providing fluid through the second lumen 915 of the endoscope 900. The fluid may be used to clean the biopsy site or used to wash the accumulated tissue samples through the suction tubing 235. The fluid may enter the biopsy forceps device 200 through the fenestrations 215, 225 in the jaws 210, 220. The fluid entering the biopsy forceps device is drawn down the suction tubing 235 when suction is applied, and may aid in washing or drawing the tissue sample down the suction tubing 235. Exemplary fluids may include water, saline, drugs or any combination thereof.

Figure 15:
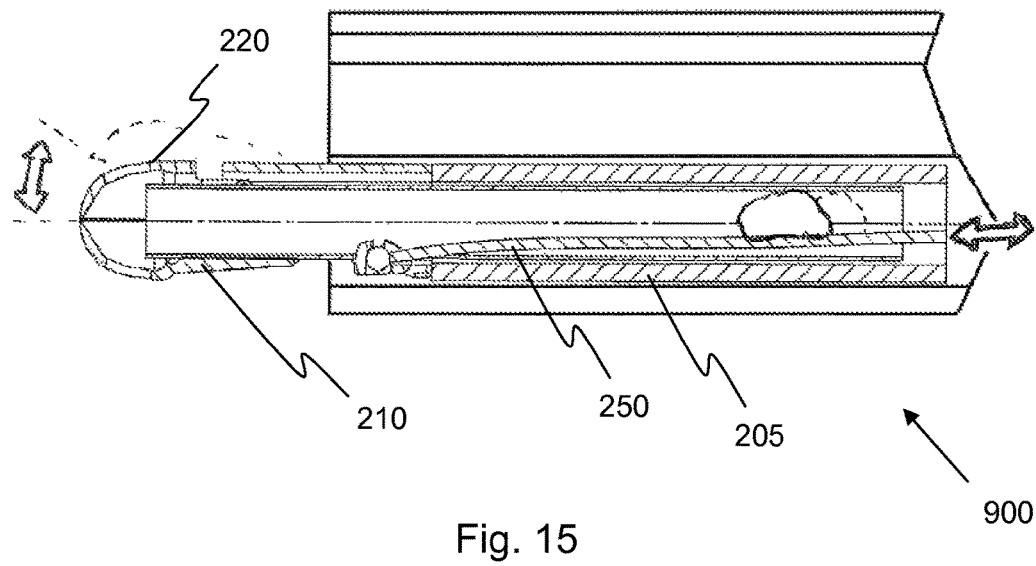
FIG. 15 is a cross-section of another alternative embodiment of a biopsy forceps device, taking a biopsy sample.

FIG. 15 illustrates a cross-section of the biopsy forceps device 200 as it extends from the endoscope 900. In this view, suction is being applied to draw a stuck tissue sample down the suction tubing 235. If the suction has failed to dislodge the stuck biopsy sample, the operator can open and close the jaws 210, 210 to dislodge the tissue sample by activating the actuation handle 400. Repeating this opening and closing action causes the wire 250 to move longitudinally within the suction tubing 235 which may then rub wire 250 against the tissue sample and aid in drawing it through the suction tubing 235. This method may be effective in dislodging a tissue sample that has become stuck, and may be performed with or without irrigation.

It should be understood that in various embodiments, many elements of the endoscopic biopsy assembly 100 can be operably configured to be flexible such as, for example, but not limited to: catheter 205, suction tubing 210, suction tubing 235, wire 250, cable 315, tubing 345, and catheter 505. Alternately, one or more of the flexible elements can be substantially rigid such as exemplary catheter 205 or any other element of assembly 100.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both" When the applicants intend to indicate "only A or B but not both" then the term "only A or B but not both" will be employed, Thus, use of the term "or" herein is the inclusive, and not the exclusive use. See, Bryan A. Garner, A Dictionary of Modern Legal Usage 624 (2d. Ed, 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

The invention claimed is:

1. A biopsy device configured to be used with an endoscope, the biopsy device comprising:
    a movable first jaw having a distal arm and a lever arm;
    a stationary jaw having a distal portion and a proximal arm, wherein the first jaw is pivotally connected to the stationary jaw at a pivot and the lever arm is disposed proximal of the pivot when the first jaw is closed, and movement of the first jaw in the open direction is prohibited at a fully open position by a ledge on the stationary jaw, wherein the ledge extends radially outwardly from surrounding portions of the stationary jaw and defines an arc through which the first jaw pivots and is dimensioned so as to not interfere with the pivoting of the first jaw;
    a catheter extending proximally from the first jaw and stationary jaw;
    a suction tube disposed within the catheter and extending distally beyond the pivot, wherein the suction tube is disposed within the first jaw and the stationary jaw with each jaw in a closed position; and
    a wire having a distal end connected to the lever arm of the first jaw and a proximal end connected to an actuation mechanism, and having a length at least partially disposed within the catheter;
    wherein a portion of the lever arm surrounds a side of the stationary jaw opposite the distal arm and a longitudinal axis of the lever arm of the first jaw is defined from the pivot to a place that the wire connects the first jaw;
    wherein the distal arm of the first jaw defines a first aperture, and the distal portion of the stationary jaw defines a second aperture, and the first aperture and the second aperture define an axis of travel through the biopsy device;
    wherein an angle between a longitudinal axis of the distal portion of the stationary jaw and a longitudinal axis of the distal arm of the first jaw is less than 90 degrees, when the first jaw contacts the ledge, and
    wherein the longitudinal axis of the lever arm is substantially perpendicular to a longitudinal axis of the catheter, when the first jaw contacts the ledge.

2. The biopsy device of claim 1, further comprising a collection chamber operatively connected to the catheter.

3. The biopsy device of claim 2, wherein the collection chamber is configured to be connected to the actuation mechanism.

4. The biopsy device of claim 1, wherein at least one of the first jaw and the stationary jaw is operably configured to deliver radio frequency energy to tissue.

5. The biopsy device of claim 1, wherein the wire of the biopsy device is operably configured to deliver radio frequency energy to at least one of the first jaw and the stationary jaw.

6. The biopsy device of claim 1, wherein the first aperture and the second aperture define an axis of travel perpendicular to the longitudinal axis of the catheter.

7. The biopsy device of claim 1, wherein the wire has a length at least partially disposed within the suction tube.

8. The biopsy device of claim 1, wherein the entire length of the wire is disposed outside of the suction tube.

9. The biopsy device of claim 8, wherein the suction tube includes at least one groove on an outside surface, the at least one groove extending from a distal end of the suction tube and aligned with a containment portion of the catheter.

10. The biopsy device of claim 1, wherein the wire comprises a ball disposed at the distal end of the wire, the lever arm comprises a socket disposed at a proximal portion of the lever arm, the ball engages the socket such that the ball remains housed in the socket during operation of the biopsy device, the wire is configured to push or pull the lever arm.

* * * * *